United States Patent [19]

Horodysky

[11] Patent Number: 4,524,005
[45] Date of Patent: Jun. 18, 1985

[54] BORATED DIHYDROCARBYLENETRIAMINE AMIDES AND LUBRICANT AND FUEL COMPOSITIONS CONTAINING SAME

[75] Inventor: Andrew G. Horodysky, Cherry Hill, N.J.

[73] Assignee: Mobil Oil Corporation, New York, N.Y.

[21] Appl. No.: 576,180

[22] Filed: Feb. 1, 1984

[51] Int. Cl.$^3$ ............................................. C10M 1/54
[52] U.S. Cl. ...................................... 252/49.6; 564/8; 564/9; 564/141; 564/215; 260/404.5; 260/462 R; 260/413
[58] Field of Search ...................... 252/49.6; 564/8, 9, 564/141, 215; 260/404.5 PA, 462 R, 413 R

[56] References Cited

U.S. PATENT DOCUMENTS

| | | | |
|---|---|---|---|
| 2,453,057 | 11/1948 | Zienty | 564/141 |
| 3,000,916 | 9/1961 | Klass et al. | 252/49.6 |
| 4,226,734 | 10/1980 | Schuster | 252/49.6 |
| 4,328,113 | 5/1982 | Horodysky et al. | 252/49.6 |

*Primary Examiner*—William R. Dixon, Jr.
*Assistant Examiner*—C. Johnson
*Attorney, Agent, or Firm*—Alexander J. McKillop; Michael G. Gilman; Van D. Harrison, Jr.

[57] ABSTRACT

Borated hydrocarbylenetriamine amides can be made by borating the appropriate reaction product of a triamine and an organic monocarboxylic acid. They demonstrate friction reducing and/or fuel consumption reducing properties when formulated into lubricants, particularly lubricating oils, and fuels.

26 Claims, No Drawings

4,524,005

BORATED DIHYDROCARBYLENETRIAMINE AMIDES AND LUBRICANT AND FUEL COMPOSITIONS CONTAINING SAME

CROSS REFERENCE TO RELATED APPLICATIONS

U.S. application Ser. No. 576,227, filed Feb. 1, 1984, uses the same reactants as disclosed herein, but the products disclosed are not the same. The invention claimed in Ser. No. 576,227 constitutes a product in which the amount of boron is limited to that required to react from about 5 to 95% of the amino groups present in the amine.

BACKGROUND OF THE INVENTION

1. Field of the Invention

The invention relates to novel products and to their use in lubricants or liquid fuels to reduce friction and fuel consumption in an internal combustion engine. More particularly, the invention relates to borated N-hydrocarbyl dihydrocarbylenetriamine amides and to lubricant and fuel compositions containing same.

2. Discussion of Prior Related Disclosures

As those skilled in this art know, additives impart special properties to lubricants. They may give the lubricants new properties or they may enhance properties already present. One property all lubricants have in common is the reduction of friction between materials in contact. Nonetheless, the art constantly seeks new materials to enhance such friction properties.

A lubricant, even without additives, when used in an internal combustion engine will not only reduce friction, but in the process will also reduce consumption of the fuel required to run it. When oils appeared to be inexhaustible, and cheap, minimum attention was given to developing additives for the specific purpose of increasing frictional properties or reducing fuel consumption. Instead, most of the advances in this area came as a result of additives being placed in lubricants for other purposes. However, recent events have added impetus to research programs designed specifically to find materials capable of enhancing the ability of lubricant to reduce friction.

It is probably generally understood in this art that there is not necessarily a correlation between friction reducing properties of an additive and its ability to correspondingly further reduce fuel consumption in an engine. That is, one cannot predict with absolute certainty from the ability of an additive to reduce friction that it will also act to decrease fuel consumption. Thus, even though the use of amides in lubricants is known (see U.S. Pat. No. 3,884,822, for example, which discloses lubricants containing the product of reaction between an aminopyridine and oleic acid), no art teaches or suggests the amides of this invention or that they are useful for the purposes disclosed herein.

SUMMARY OF THE INVENTION

In accordance with the invention there is provided a lubricant or liquid fuel composition comprising a major proportion of a lubricant or fuel and an antifriction amount of a product of reaction between (1) a boron compound, (2) a N-hydrocarbyl dihydrocarbylenetriamine, or a mixture of such triamines, of the formula

R—NH—R$^1$—NH—R$^1$—NHR wherein R is hydrogen or a $C_{10}$ to $C_{30}$ hydrocarbyl group, at least one of R being the latter and R$^1$ is a $C_2$ to $C_4$ hydrocarbylene group, preferably an alkylene group such as an ethylene, propylene or butylene group and (3) a carboxylic acid having the formula

R$^3$COOR$^4$ wherein R$^3$ and R$^4$ are individually selected from hydrogen and a $C_1$ to $C_4$ hydrocarbyl group, including alkyl groups, i.e., a methyl, ethyl, propyl and butyl group.

As used herein, "hydrocarbyl" and "hydrocarbylene" are preferably alkyl and alkylene, respectively, but may include alkenyl and alkenylene. "Hydrocarbyl" also may include aryl, alkaryl, aralkyl and cycloalkyl groups, the aryl portions having 6 to 14 carbon atoms.

The invention also provides the products per se and a method of reducing fuel consumption in internal combustion engines by employing the disclosed fuel or lubricant compositions.

DESCRIPTION OF SPECIFIC EMBODIMENTS

To make the additives of this invention, the N-hydrocarbyl dihydrocarbylenetriamine is reacted with the carboxylic acid or acid ester to form a compound of the formula $$\begin{array}{ccccc} R-N-R^1-N-R^1-N-R \\ | & | & | \\ R^2 & R^2 & R^2 \end{array}$$

wherein R and R$^1$ are as described herein and R$^2$ is hydrogen or a $$\begin{array}{c} R^3C- \\ \| \\ O \end{array}$$

group, at least one of R$^2$ being the latter group, in which R$^3$ is hydrogen or a $C_1$ to $C_4$ hydrocarbyl group, followed by reaction with a boron compound. In the initial reaction (amine and acid) some cyclization may also occur, but in general it does not detract from the value of the final borated products as antifriction agents.

The products of the invention prepared by the method just generally described can be made simply by heating a mixture of triamine and organic monocarboxylic acid or acid ester at a temperature and for a time to form the amide and by reacting the resulting product with a boron compound. In general, the amide is made by reacting the appropriate triamine with an acid or acid ester of the formula:

R$^3$COOR$^4$ wherein R$^3$ is as hereinabove described and R$^4$ has the same definition as R$^3$, although the two may be different. A typical acid is preferably formic acid, and less preferably is acetic, propionic or butyric acid.

The general reaction conditions are not critical. Reaction can take place between the triamine and the acid at a temperature of between about 80° C. and about 120° C., preferably about 100° C. to about 180° C. The reaction will usually be completed in from 2 to 10 hours, but where the reactants demand it, up to 24 hours may be required for reaction completion. Proportions of reactants (i.e., amine and acid) are selected so that from about 5% to about 90% of the available nitrogen groups are converted to the amide.

Hydrocarbon solvents, or other inert solvents may be used in the reaction. Included among the useful solvents are benzene, toluene and xylene. In general, any hydrocarbon solvent can be used in which the reactants are soluble and which can, if the products are soluble therein, by easily removed.

In carrying out the reaction, the molar ratio of triamine to acid preferably will range from about 1:1 to aboud 1:2.

Some of the useful triamines include N-oleyl diethylenetriamine, N-tallow diethylenetriamine, N-hydrogenated tallow diethylenetriamine, N-soya diethylenetriamine, N-coco diethylenetriamine, N-decyl diethylenetriamine, N-dodecyl diethylenetriamine, N-tetradecyl diethylenetriamine, N-octadecyl diethylenetriamine, N-eicosyl diethylenetriamine, N-triacontyl diethylenetriamine, N-oleyl dipropylenetriamine, N-tallow dipropylenetriamine, N-hydrogenated tallow dipropylenetriamine, N-soya dipropylenetriamine, N-coco dipropylenetriamine, N-decyl dipropylenetriamine, N-dodecyl dipropylenetriamine, N-tetradecyl dipropylenetriamine, N-octadecyl dipropylenetriamine, N-eicosyl dipropylenetriamine, N-triacontyl dipropylenetriamine, the corresponding N—$C_{10}$ to $C_{30}$ hydrocarbyl dibutylenetriamine members as well as the corresponding mixed members, as for example, the N—$C_{10}$ to $C_{30}$ hydrocarbyl ethylenepropylenetriamine, N—$C_{10}$ to $C_{30}$ hydrocarbyl ethylenebutylenetriamine and N—$C_{10}$ to $C_{30}$ hydrocarbyl propylenebutylenetriamine. All the R groups mentioned are alkyl or alkenyl. Others, such as an aryl group, an alkaryl group, an aralkyl group or a cycloalkyl group, as previously mentioned, may be used in effective additives.

The boron compounds that may be used in the herein-described invention include boric oxide, metaborates, a compound of the formula

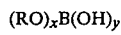
$(RO)_xB(OH)_y$ wherein R is an alkyl group containing 1 to 6 carbon atoms, x is 0 to 3 and y is 0 to 3, their sum being 3, and mixtures of any of these boron compounds. The formula embraces boric acid as well as the alkylborates, e.g., mono-, di- and trimethyl borates, mono-, di- and tripropyl borates, mono-, di- and triaryl borates and mono-, di- and trihexyl borates.

At least 5% of the nitrogen sites available for boration are reacted with the appropriate boron compound. Up to 100% thereof may be reacted or, if desired an excess of boron compound may be used to produce an "overborated" product. In these ways, one obtains a reaction product containing from about 0.1% to about 10% by weight of boron.

Just as with the reaction to form the amide, the reaction conditions are not critical in the boration reaction. Reaction temperatures can range from about 80° C. to about 260° C., preferably about 120° C. to 170° C. Times of reaction will generally be for from about 1 to about 20 hours. Solvents that can be used include hydrocarbon solvents cuch as benzene, toluene and xylene as well as alcohol solvents such as butanol and pentanol.

An important feature of the invention is the ability of the additives to improve the friction qualities of oleaginous materials such as lubricating oils, which may be either a mineral oil a synthetic oil, or mixtures thereof, or a grease in which any of the aforementioned oils are employed as the vehicle. In general, mineral oils, both paraffinic, naphthenic or mixtures thereof, are employed as a lubricating oil or as the grease vehicle, they may be of any suitable lubricating viscosity range, as for example, from about 45 SSR at 100° F. to about 6000 SSU at 100° F., and preferably from about 50 to about 250 SSR at 210° F. These oils may have viscosity indexes ranging to about 100 or higher. Viscosity indexes from about 70 to about 95 are preferred. The average molecular weights of these oils may range from about 250 to about 800. Where the lubricant is to be employed in the form of grease, the lubricating oil is generally employed in an amount sufficient to balance the total grease composition, after accounting for the desired quantity of the thickening agent, and other additive components to be included in the grease formulation. A wide variety of materials may be employed as thickening or gelling agents. These may include any of the conventional metal salts or soaps, which are dispersed in the lubricating vehicle in grease-forming quantities in an amount to impart to the resulting grease composition the desired consistency. Included are metal soaps of hydroxystearates, derived 12-hydroxystearic acid, esters or glycerides, such as lithium or calcium, 12-hydroxystearate. Often preferred is the lithium 12-hydroxystearate. Other thickening agents that may be employed in the grease formulation may comprise the non-soap thickeners, such as surface-modified clays and silicas, aryl ureas, calcium complexes and similar materials. In general, grease thickeners may be employed which do not melt and dissolve when used at the required temperature within a particular environment; however, in all other respects, any material which is normally employed for thickening or gelling hydrocarbon fluids for forming grease can be used in preparing the aforementioned improved grease in accordance with the present invention.

In instances where synthetic oils are desired, various classes of oils may be successfully utilized. Typical synthetic vehicles include polyisobutylenes, polybutenes, hydrogenated polydecenes, polypropylene glycol, polyethylene glycol, trimethylol propane esters, neopentyl and pentaerythritol esters, di(2-ethylhexyl)-sebacate, di(2-ethylhexyl)adipate, dibutyl phthalate, fluorocarbons, silicate esters, silanes, esters of phosphorus-containing acids, liquid ureas, ferrocene derivatives, hydrogenated synthetic oils, chain-type polyphenyls, siloxanes and silicones (polysiloxanes) and alkyl-substituted diphenyl ethers typified by a butyl-substituted bis(p-phenoxy phenyl)ether, phenoxy phenylethers. In preparing greases using synthetic oils, thickeners known to the art (including some of those mentioned hereinabove) can be used.

It is to be understood that the lubricant compositions contemplated herein can also contain other materials. For example, other corrosion inhibitors, extreme pressure agents, viscosity index improvers, coantioxidants, antiwear agents and the like can be used. These include, but are not limited to, phenates, sulfonates, succinimides, zinc dialkyl dithiophosphates, and the like. These materials do not detract from the value of the compositions of this invention; rather the materials serve to impart their customary properties to the particular compositions in which they are incorporated. In particular, the frictional and high temperature stabilizing properties of the compositions of this invention may be enhanced by the incorporation of from about 0.1% to about 2% by weight of metal phosphorodithioates, particularly zinc dialkyl dithiophosphates, made from low to moderate molecular weight alcohols such as propanol, butanol, pentanol, hexanol, octanol and the like, and mixtures thereof.

The products of this invention can also be employed in liquid hydrocarbon fuels, alcohol fuels or mixtures thereof, including mixtures of hydrocarbons, mixtures of alcohols and mixtures of hydrocarbon and alcohol fuels to reduce friction and improve fuel economy. About 25 pounds to about 500 pounds or preferably about 50 to 100 pounds, of amide per thousand barrels of fuel for internal combustion engines may be used. Liquid hydrocarbon fuels include gasoline, gasahol, fuel oils and diesel oils. Methyl and ethyl alcohols are examples of alcohol fuels. Other additives such as fuel dispersants, carburetor, detergents, stabilizers, antirust agents, demulsifiers metal deactivators, intake manifold detergents, dyes and the like can be used with our friction reducers in the fuel compositions.

In general, the reaction products of the present invention may be employed in any amount which is effective for imparting the desired degree of friction reduction and resulting fuel economy improvement and/or antioxidant activity. In lubricant applications, the product is effectively employed in amounts from about 0.05% to about 10% by weight, and preferably from about 0.5% to about 5% of the total weight of the composition.

The following Examples will present illustrations of the invention. They are illustrative only, and are not meant to limit the invention.

EXAMPLE 1

Approximately 110 g of N-oleyl dipropylenetriamine (obtained as Triamine OL from Armak Chemical Co.), 100 g of toluene and 13 g of 88% formic acid were charged to a 1 liter flask equipped with heater, agitator, Dean-Stark tube with condenser and a means to blanket the vapor space with nitrogen. The reaction mixture was slowly heated 180° C. over a period of 6 hours until water evolution as a result of azeotropic distillation ceased. The solvent was removed by vacuum distillation at 180° C.

EXAMPLE 2

Approximately 82 g of the N-oleyl-dipropylenetriamine formic acid reaction product of Example 1 were charged to a 500 ml reactor equipped with heater, agitator, Dean-Stark tube with condenser and a means to blanket the vapor space with nitrogen. Approximately 80 g of toluene and 8 g of boric acid were added and the reactor contents were heated up to 155° C. over a period of 5 hours until water evolution as a result of azeotropic distillation ceased. The crude product was vacuum topped at 155° C. to remove solvent. After cooling to about 100° C., the product was filtered through diatomaceous earth.

EVALUATION OF THE COMPOUNDS

The compounds were evaluated in Low Velocity Friction Apparatus (LVFA) in a fully formulated mineral or synthetic, automotive engine oil containing an additive package including antioxidant, dispersant and detergent, and metallic dithiophosphate. Although evaluation of additives was performed in lubricant formulations, these results correlate well with expected frictional and fuel economy improvements when these same additives are used in fuels burned in internal combustion engines. For example, this test generally predicts the reduction in friction of the piston rings moving against the cylinder walls that have been wetted by the additive blended into the fuel. The resulting reduction in friction observed, if any, may translate into an improvement in economy of the fuel actually consumed. Additionally, these additives when used in fuels, may actually help reduce wear of the internal combustion engine parts.

Description

The Low Velocity Friction Apparatus (LVFA) is used to measure the coefficient of friction of test lubricants under various loads, temperatures, and sliding speeds. The LVFA consists of a flat SEA 1020 steel surface (diameter 1.5 in.) which is attached to a drive shaft and rotated over a stationary, raised, narrow ringed SAE 1020 steel surface (area 0.08 in.$^2$. Both surfaces are submerged in the test lubricant. Friction between the steel surfaces is measured as a function of the sliding speed at a lubricant temperature of 250° F. The friction between the rubbing surfaces is measured using a torque arm-strain gauge system. The strain gauge output, which is calibrated to be equal the the coefficient of friction, is fed to the Y axis of an X-Y plotter. The speed signal from the tachometer-generator is fed to the X-axis. To minimize external friction, the piston is supported by an air bearing. The normal force loading the rubbing surfaces is regulated by air pressure on the bottom of the piston. The drive system consists of an infinitely variable-speed hydraulic transmission driven by a ½ HP electric motor. To vary the sliding speed, the output speed of the transmission is regulated by a lever-cammotor arrangement.

Procedure

The rubbing surfaces and 12–13 ml of test lubricants are placed on the LVFA. A 240 psi load is applied and the sliding speed is maintained at 40 fpm at ambient temperature for a few minutes. A plot for coefficients of friction ($U_k$) vs. speed were taken at 240, 300, 400, and 500 psi. Freshly polished steel specimens are used for each run. The surface of the steel is parallel ground to 4 to 8 microinches. The results in Table 1 refer to percent reduction infriction compared to the unmodified oil. That is, the formulation mentioned above was tested without the compound of this invention and this became the basis for comparison. The results were obtained at 250° F. and 500 psi.

TABLE 1

Evalution of Frictional Properties Using the Low Velocity Friction Apparatus

| | Conc. in Test Oil Wt. % | Percent Reduction In Coefficient of Friction | |
|---|---|---|---|
| | | 5 Ft./ Min. | 30 Ft./ Min. |
| Base Oil A - Fully formulated synthetic automotive engine oil containing detergent/dispersant/ inhibitor performance package SAE 5W-30 | — | 0 | 0 |
| Example 2 - Plus Base Oil | 2 | 36 | 39 |

TABLE 2

Evaluation of Friction Properties Using Low Velocity Friction Apparatus

| | Conc. In Test Wt. % | Percent Reduction in Coefficient of Friction | |
|---|---|---|---|
| | | 5 Ft./ Min. | 30 Ft./ Min. |
| Base Oil B - Fully formulated mineral oil based automotive engine oil containing detergent/dispersant/inhibitor package - SAE 10W-40 | — | 0 | 0 |
| Example 2 - Plus Base Oil | 2 | 32 | 28 |

The high oxidation stability of the additives was determined by evaluation of additive blends in 200 second solvent paraffinic neutral lubricating oil using the Catalytic Oxidation Test at 325° F. for 40 hours as shown in Table 3. This test is run by selecting the appropriate composition, placing it in a suitable vessel and bubbling air through it at the appropriate temperature and for the prescribed time. The sample has added to it small amounts of metals commonly associated with engines, i.e., iron, copper, aluminum and lead.

I claim:

1. A product of reaction made by (1) reacting an amine or a mixture of amines of the formula $$R-NH-R^I-NH-R^I-NHR$$

wherein R is hydrogen or a $C_{10}$ to $C_{30}$ hydrocarbyl group, at least one R being the latter, and $R^I$ is the same or different $C_2$ to $C_4$ hydrocarbylene group with a carboxylic acid or ester of the formula $$R^2COOR^3$$

wherein $R^2$ and $R^3$ are individually hydrogen or a $C_1$ to $C_4$ hydrocarbyl group, (2) followed by reacting the product of (1) with a boron compound selected from the group consisting of boric oxide, a metaborate, a compound of the formula $$(RO)_xB(OH)_y$$

wherein R is a $C_1$ to $C_6$ alkyl group and x and y are 0 to 3, their sum being 3, and mixtures thereof, the amount of acid or ester reacted with the amine being sufficient to react from about 5% to about 95% of the available amino groups and the amount of boron compound reacted with the product from reaction (1) being in excess of the remaining amount required to react with the amino groups.

2. The product of claim 1 wherein R is hydrogen, alkyl, alkenyl, aryl, alkaryl, aralkyl or cycloalkyl, and wherein at least one R is not hydrogen.

3. The product of claim 1 wherein $R^I$ is an ethylene group, a propylene group or a butylene group.

4. The product of claim 1 wherein $R^2$ and $R^3$ individually are a $C_1$ to $C_4$ hydrocarbyl group.

5. The product of claim 4 wherein the hydrocarbyl group is a methyl, ethyl, propyl or butyl group.

6. The product of claim 1 wherein the amine is N-oleyl diethylenetriamine, N-tallow diethylenetriamine, N-hydrogenated tallow diethylenetriamine, N-soya diethylenetriamine, N-coco diethylenetriamine, N-decyl diethylenetriamine, N-dodecyl diethylenetriamine, N-tetradecyl diethylenetriamine, N-octadecyl diethylenetriamine, N-eicosyl diethylenetriamine, N-triacontyl diethylenetriamine, N-oleyl dipropylenetriamine, N-tallow dipropylenetriamine, N-hydrogenated tallow dipropylenetriamine, N-soya dipropylenetriamine, N-coco dipropylenetriamine, N-decyl dipropylenetriamine, N-dodecyl dipropylenetriamine, N-tetradecyl dipropylenedtriamine, N-octadecyl dipropylenetriamine, N-eicosyl dipropylenetriamine, N-triacontyl dipropylenetriamine, the corresponding N—$C_{10}$ to $C_{30}$ hydrocarbyl dibutylenetriamine members, mixed N—$C_{10}$ to $C_{30}$ hydrocarbyl ethylenepropylenetriamine, mixed N—$C_{10}$ to $C_{30}$ hydrocarbyl ethylenebutylenetriamine or mixed N—$C_{10}$ to $C_{30}$ hydrocarbyl propylenebutylenetriamine.

7. The product of claim 5 wherein the acid is formic acid, acetic acid, propionic acid, butyric acid or mixtures thereof.

8. The product of claim 1 wherein the boron compound is a metaborate, boric oxide, boric acid, mono-, di- or trimethyl borate, mono-, di- or triethyl borate, mono-, di- or tripropyl borate, mono-, di- or tributyl borate, mono-, di- or triamyl borate or mono-, di- or trihexyl borate.

9. The product of claim 8 wherein the boron compound is boric acid.

10. The product of claim 1 wherein the amine is N-tallow-dipropylenetriamine, the boron compound is boric acid and the carboxylic acid is formic acid.

11. A lubricant composition comprising a major amount of a lubricating oil or grease therefrom and an antifriction amount of a product of reaction made by (1) reacting an amine or a mixture of amines of the formula $$R-NH-R^I-NH-R^I-NHR$$

wherein R is hydrogen or a $C_{10}$ to $C_{30}$ hydrocarbyl group, at least one R being the latter, and $R^I$ is the same or different $C_2$ to $C_4$ hydrocarbylene group with a carboxylic acid or ester of the formula $$R^2COOR^3$$

wherein $R^2$ and $R^3$ are individually hydrogen or a $C_1$ to $C_4$ hydrocarbyl group, followed by reacting the product of (1) with a boron compound selected from the group consisting of boric oxide, a metaborate, a compound of the formula $$(RO)_xB(OH)_y$$

wherein R is a $C_1$ to $C_6$ alkyl group and x and y are 0 to 3, their sum being 3, and mixtures thereof, the amount of acid or ester reacted with the amine being sufficient to react from about 5% to about 95% of the available amino groups and the amount of boron compound reacted with the product from reaction (1) being in excess of the remaining amount required to react with the amino groups.

12. The composition of claim 11 wherein R is hydrogen, alkyl, alkenyl, aryl, alkaryl, aralkyl or cycloalkyl, and wherein at least one R is not hydrogen.

13. The composition of claim 11 wherein $R^I$ is an ethylene group, a propylene group or a butylene group.

14. The composition of claim 11 wherein $R^2$ and $R^3$ are individually a $C_1$ to $C_4$ hydrocarbyl group.

15. The composition of claim 14 wherein the hydrocarbyl group is a methyl, ethyl, propyl or butyl group.

16. The composition of claim 11 wherein the amine is N-oleyl diethylenetriamine, N-tallow diethylenetriamine, N-hydrogenated tallow diethylenetriamine, N-soya diethylenetriamine, N-coco diethylenetriamine, N-decyl diethylenetriamine, N-dodecyl diethylenetriamine, N-tetradecyl diethylenetriamine, N-octadecyl diethylenetriamine, N-eicosyl diethylenetriamine, N-triacontyl diethylenetriamine, N-oleyl dipropylenetriamine, N-tallow dipropylenetriamine, N-hydrogenated tallow dipropylenetriamine, N-soya dipropylenetriamine, N-coco dipropylenetriamine, N-decyl dipropylenetriamine, N-dodecyl dipropylenetriamine, N-tetradecyl dipropylenedtriamine, N-octadecyl dipropylenetriamine, N-eicosyl dipropylenetriamine, N-triacontyl dipropylenetriamine, the corresponding N—$C_{10}$ to $C_{30}$ hydrocarbyl dibutylenetriamine members, mixed N—$C_{10}$ to $C_{30}$ hydrocarbyl ethylenepropylenetriamine, mixed N—$C_{10}$ to $C_{30}$ hydrocarbyl ethylenebutylenetriamine or mixed N—$C_{10}$ to $C_{30}$ hydrocarbyl propylenebutylenetriamine.

17. The composition of claim 15 wherein the acid is formic acid, acetic acid, propionic acid, butyric acid or mixtures thereof.

18. The composition of claim 11 wherein the boron compound is a metaborate, boric oxide, boric acid, mono-, di- or trimethyl borate, mono-, di- or triethyl borate, mono-, di- or tripropyl borate, mono-, di- or tributyl borate, mono-, di- or triamyl borate or mono-, di- or trihexyl borate.

19. The composition of claim 18 wherein the boron compound is boric acid.

20. The composition of claim 11 wherein the amine is N-tallow-dipropylenetriamine, the boron compound is boric acid and the carboxylic acid is formic acid.

21. The composition of claim 11 wherein the lubricant is (1) a mineral oil, (2) a synthetic oil or a mixture of synthetic oils, (3) a mixture of (1) and (2) and (4) a grease from (1), (2) or (3).

22. The composition of claim 21 wherein the lubricant is a mineral oil.

23. The composition of claim 21 wherein the lubricant is a synthetic oil or mixture of synthetic oils.

24. The composition of claim 21 wherein the lubricant is a mixture of (1) and (2).

25. The composition of claim 21 wherein the lubricant is said grease.

26. A method of reducing fuel consumption in an internal combustion engine comprising lubricating said engine with a lubricating oil composition comprising a major proportion of a lubricating oil and a fuel consumption reducing amount of a product of reaction made by (A) reacting an amine or a mixture of amines of the formula $$R-NH-R^I-NH-R^I-NHR$$

wherein R is hydrogen or a $C_{10}$ to $C_{30}$ hydrocarbyl group, at least one R being the latter, and $R^I$ is the same or different $C_2$ to $C_4$ hydrocarbylene group with a carboxylic acid or ester of the formula $$R^2COOR^3$$

wherein $R^2$ and $R^3$ are individually hydrogen or a $C_1$ to $C_4$ hydrocarbyl group, (B) and reacting the product of (A) with a boron compound selected from the group consisting of boric oxide, a metaborate, a compound of the formula $$(RO)_xB(OH)_y$$

wherein R is a $C_1$ to $C_6$ alkyl group and x and y are 0 to 3, their sum being 3, and mixtures thereof, the amount of acid or ester reacted with the amine being sufficient to react from about 5% to about 90% of the available amino groups and the amount of boron compound reacted with the product from reaction (A) being in excess of the remaining amount required to react with the amino groups.

* * * * *